(12) United States Patent
Babaeizadeh et al.

(10) Patent No.: US 10,085,687 B2
(45) Date of Patent: *Oct. 2, 2018

(54) METHOD AND APPARATUS FOR PROVIDING A VISUAL REPRESENTATION OF SLEEP QUALITY BASED ON ECG SIGNALS

(71) Applicant: KONINKLIJKE PHILIPS N.V., Eindhoven (NL)

(72) Inventors: Saeed Babaeizadeh, Arlington, MA (US); Sophia Huai Zhou, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/424,294

(22) Filed: Feb. 3, 2017

(65) Prior Publication Data

US 2017/0143255 A1    May 25, 2017

Related U.S. Application Data

(63) Continuation of application No. 14/385,192, filed as application No. PCT/IB2013/052142 on Mar. 18, 2013, now Pat. No. 9,566,032.

(Continued)

(51) Int. Cl.
*A61B 5/0402* (2006.01)
*A61B 5/044* (2006.01)
(Continued)

(52) U.S. Cl.
CPC .......... *A61B 5/4815* (2013.01); *A61B 5/0006* (2013.01); *A61B 5/0402* (2013.01);
(Continued)

(58) Field of Classification Search
CPC .............. A61B 5/0006; A61B 5/04012; A61B 5/04014; A61B 5/0402; A61B 5/044; A61B 5/4815; A61B 5/7253; A61B 5/7257

See application file for complete search history.

(56) References Cited

U.S. PATENT DOCUMENTS

2003/0055348 A1    3/2003  Chazal et al.
2005/0256418 A1   11/2005  Mietus et al.
(Continued)

FOREIGN PATENT DOCUMENTS

JP    2009078139 A    4/2009
TW    I289062 B2      11/2007

OTHER PUBLICATIONS

Mietus et al, "Detection of Obstructive Sleepl Apnea From Cardiac Interbeat Interval Time Series", Computers in Cardiology, vol. 27, 2000, p. 753-756.

(Continued)

*Primary Examiner* — Allen Porter, Jr.

(57) ABSTRACT

A method of providing a graphical representation of sleep quality includes obtaining ECG data for a patient, obtaining a plurality of N-N intervals from the ECG data, calculating a plurality of spectral densities based on the plurality of N-N intervals, wherein each spectral density is associated with one of a plurality of successive time windows and is calculated based on certain ones of the N-N intervals associated with the one of the plurality of successive time windows, and generating the graphical representation of sleep quality using the plurality of spectral densities.

23 Claims, 6 Drawing Sheets

Related U.S. Application Data

(60) Provisional application No. 61/613,637, filed on Mar. 21, 2012.

(51) Int. Cl.
*A61B 5/0452* (2006.01)
*A61B 5/00* (2006.01)
*A61B 5/04* (2006.01)
*A61B 5/0428* (2006.01)
*A61B 5/0432* (2006.01)

(52) U.S. Cl.
CPC .......... *A61B 5/044* (2013.01); *A61B 5/04014* (2013.01); *A61B 5/0432* (2013.01); *A61B 5/0452* (2013.01); *A61B 5/04286* (2013.01); *A61B 5/4806* (2013.01); *A61B 5/7257* (2013.01)

(56) References Cited

U.S. PATENT DOCUMENTS

| | | |
|---|---|---|
| 2005/0267362 A1 | 12/2005 | Mietus et al. |
| 2006/0041201 A1 | 2/2006 | Behbehani et al. |
| 2006/0235315 A1 | 10/2006 | Akselrod et al. |
| 2006/0287605 A1 | 12/2006 | Lin |
| 2007/0032733 A1 | 2/2007 | Burton |
| 2008/0045815 A1 | 2/2008 | Derchak |
| 2008/0058659 A1 | 3/2008 | Al-Abed et al. |
| 2010/0069762 A1 | 3/2010 | Mietus et al. |
| 2011/0124979 A1 | 5/2011 | Heneghan et al. |
| 2011/0160603 A1 | 6/2011 | Langston et al. |

OTHER PUBLICATIONS

Thomas, "Differentiating Obstructive From Central and Complex Sleep Apena Using an Automated Electrocardiogram-Based Method", Sleep, vol. 30, No. 12, 2007, p. 1756-1769.

Mendez et al, "Sleep Apena Screening by Autoregressive Modesl From a Single ECG Lead", IEEE Tranactions on Biomedical Engineering, vol. 56, No. 12, 2009, p. 2838-2850.

METHOD AND APPARATUS FOR PROVIDING A VISUAL REPRESENTATION OF SLEEP QUALITY BASED ON ECG SIGNALS

BACKGROUND OF THE INVENTION

1. Field of the Invention

The present invention pertains to sleep disorder assessment and reporting, and, in particular, to a method and apparatus for generating and providing a visual representation of sleep quality based on electrocardiogram (ECG) signals.

2. Description of the Related Art

Sleep-Disordered breathing (SDB) describes a group of disorders characterized by abnormal respiratory patterns or the quantity of ventilation during sleep. It is a highly prevalent disease that remains under diagnosed.

Obstructive sleep apnea (OSA), the most common such disorder, is characterized by the repetitive complete or partial collapse of the pharyngeal airway during sleep and the need to arouse to resume ventilation. OSA affects at least 2% to 4% of the adult population and is increasingly recognized by the public. The high prevalence and wide spectrum of severity of OSA in adults have been well documented by several population-based cohort studies conducted in the United States, Europe, Australia, and Asia. Available data indicates that OSA prevalence is 2 to 3 times higher in patients with cardiovascular disease (CVD) than in reference normal populations. In addition, population-based epidemiological studies and observations of OSA patients have consistently shown a link between OSA and hypertension, heart failure, atrial fibrillation, myocardial infarction, nocturnal sudden death, and stroke.

Another kind of SDB, called central sleep apnea (CSA), is a neurological condition which causes the loss of all respiratory effort during sleep and is also usually marked by decreases in blood oxygen saturation. CSA has been linked to increases in heart failure, left ventricular dysfunction, and stroke. Mixed sleep apnea combines components of both CSA and OSA, where an initial failure in breathing efforts allows the upper airway to collapse.

Polysomnography is a definitive diagnostic technique that may be used in patients with suspected apnea. It often requires spending a night in a sleep laboratory during which multiple physiological variables are continuously recorded. The variables generally include sleep staging to collect a number of signals using several devices including an electroencephalogram (EEG), an electromyogram (EMG), an electrooculogram (EOG), a respiration (flow, effort, oxygen saturation) detection device, and a snoring detection device. With these signals, disordered breathing, in addition to its effect on sleep and oxygenation, can be precisely quantified.

Polysomnography is expensive because it requires overnight evaluation in sleep laboratories with dedicated systems and attending personnel. The cost and relative scarcity of diagnostic sleep laboratories contribute to the fact that sleep apnea is widely under diagnosed (it is estimated that more than 85% of patients with clinically significant and treatable OSA have never been diagnosed). Hence, techniques to screen patients for SDB with fewer and simpler measurements and without the need for a specialized sleep laboratory may be of benefit.

Several different such techniques have been proposed. Examples include the Epworth Sleepiness Scale, the Berlin questionnaire, overnight oximetry, and devices combining limited respiratory assessment, ECG, and oximetry. Specialized analysis of 24-hour ECG recordings also has been proposed as a possible screening tool. The most often currently used in clinical practice is overnight oximetry. None of these techniques, however, has proven to be a viable yet simple and cost effective solution for SDB screening.

SUMMARY OF THE INVENTION

Accordingly, it is an object of the present invention to provide a SDB screening apparatus that overcomes the shortcomings of conventional devices. This object is achieved according to one embodiment of the present invention by providing a sleep quality measurement apparatus that provides a graphical representation of sleep quality based on at least one channel of ECG data.

It is yet another object of the present invention to provide a method of SDB screening that does not suffer from the disadvantages associated with conventional SDB screening techniques. This object is achieved by providing a method of generating a graphical representation of sleep quality based on at least one channel of ECG data.

In one embodiment, a method of providing a graphical representation of sleep quality is provided that includes obtaining ECG data for a patient, obtaining a plurality of N-N intervals from the ECG data, calculating a plurality of spectral densities based on the plurality of N-N intervals, wherein each spectral density is associated with one of a plurality of successive time windows and is calculated based on certain ones of the N-N intervals associated with the one of the plurality of successive time windows, and generating the graphical representation of sleep quality using the plurality of spectral densities.

In another embodiment, a sleep quality measurement apparatus is provided that includes a processing unit having one or more routines executable by the processing unit and structured to obtain a plurality of N-N intervals (40) from ECG data generated from cardiac signals collected from a patient, calculate a plurality of spectral densities based on the plurality of N-N intervals, wherein each spectral density is associated with one of a plurality of successive time windows and is calculated based on certain ones of the N-N intervals associated with the one of the plurality of successive time windows, and generate a graphical representation of sleep quality using the plurality of spectral densities.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
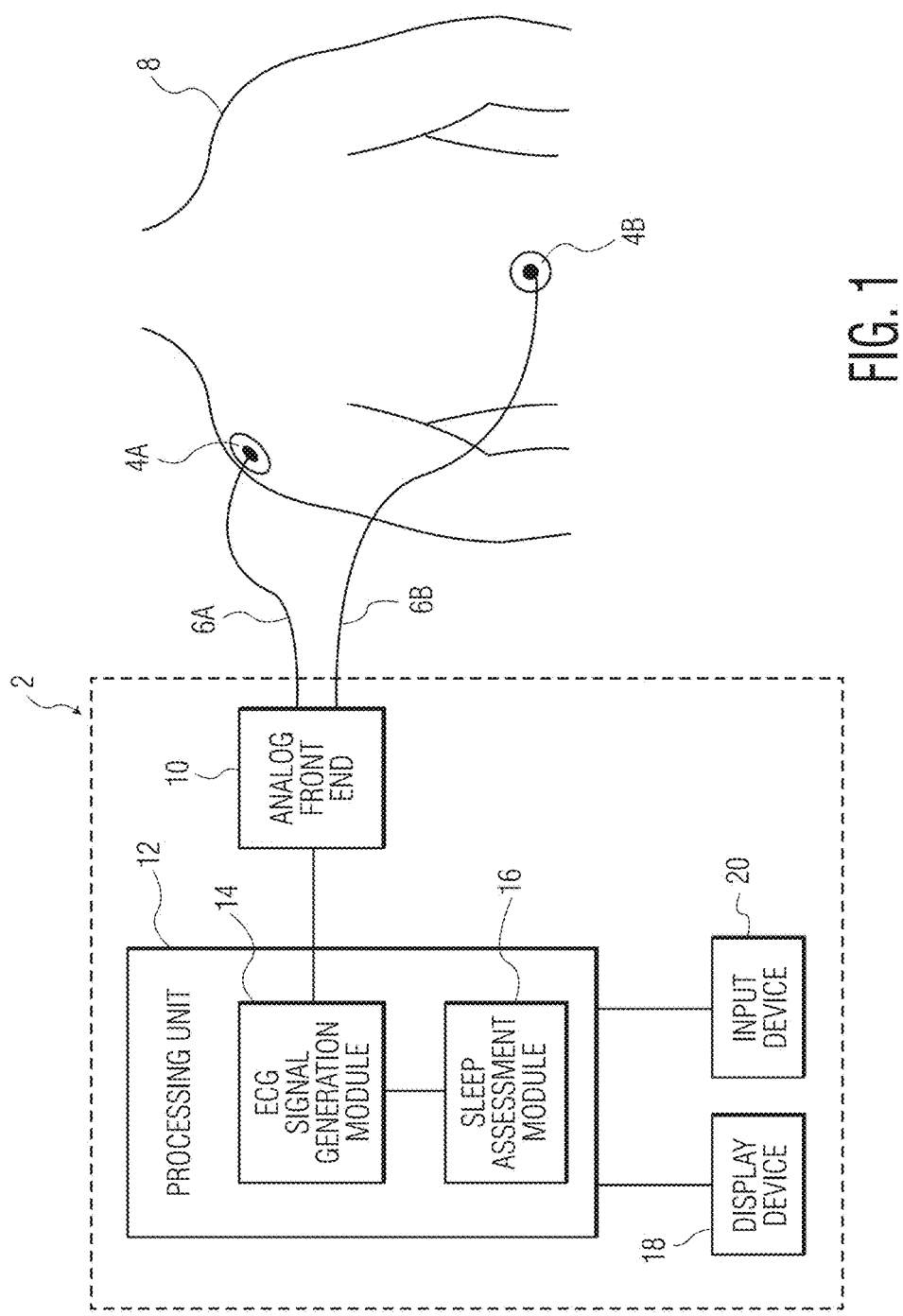
FIG. 1 is a schematic diagram showing a sleep quality measurement device according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The importance of the cardiovascular response to sleep has been recognized in the recently revised Sleep Scoring Manual from the American Association of Sleep Medicine (AASM), which now includes scoring of a continuous-lead ECG as a recommended component of polysomnography. The present invention, as described in detail herein in various exemplary embodiments, provides a method using an ECG-based technique to present and visualize sleep apnea epochs by presenting SDB in a graphical report (which in one particular embodiment may be a one page report). More specifically, the technique of the present invention employs at least one channel of ECG data collected/recorded during sleep to generate a graphical report which indicates the presence or absence of SDB episodes, including sleep apnea, by applying series of signal processing techniques to the ECG data.

Due to its non-invasive and low-cost nature, the method of the present invention has the potential for numerous applications in sleep medicine. As is known, single lead ECG is readily available for most in-hospital and at home patients. Therefore, the technique of the present invention provides a sleep apnea screening report without adding any additional cost to those monitoring techniques which already include at least one channel of ECG. It can also be an alternative solution added to a home-based multi-channel sleep apnea diagnostic device in case the device loses respiratory signals during the night. Furthermore, the technique of the present invention may be designed as a software module/tool which may be integrated inside a particular device (e.g., an ECG recorder) or be present as a stand-alone software on either the same device or on a separate device such as a personal computer.

FIG. 1 is a schematic diagram showing a sleep quality measurement device 2 according to one non-limiting, exemplary embodiment of the invention. In the illustrated, non-limiting embodiment, sleep quality measurement device 2 employs single lead/channel ECG detection and includes electrodes 4A and 4B coupled to wires 6A, 6B, respectively, for collecting cardiac signals from a patient 8. It will be understood, however, that this is meant to be exemplary only, and that present invention may employ more than single lead/channel ECG detection. For example, the present invention may collect ECG data using multiple lead techniques, such as, without limitation, known or hereafter developed three lead, five lead or twelve lead techniques. As will be appreciated, by using more than a single lead/channel, the accuracy of the ECG data may be improved (e.g., it may provide for more accurate detection of N-N intervals as described elsewhere herein). However, it will be understood that all that is needed in the present invention is a least one lead/channel of ECG data.

As seen in FIG. 1, sleep quality measurement device 2 includes an analog front end 10 to which wires 6A and 6B are connected. Analog front end 10 in the illustrated embodiment receives the analog cardiac signals collected by wires 6A and 6B via electrodes 4A, 4B, amplifies the signals and converts the signals to digital form. Sleep quality measurement device 2 further includes a processing unit 12 which receives the digital cardiac data that is output by analog front end 10. Processing unit 12 includes a microprocessor, a microcontroller, or any other suitable processor, which is operatively coupled to a suitable memory for storing routines to be executed by processing unit 12. The memory can be any of a variety of types of internal and/or external storage media such as, without limitation, RAM, ROM, EPROM(s), EEPROM(s), and the like, that provide a storage register for data storage, and can be volatile memory or nonvolatile memory. In addition, the memory, which may be separate from and/or internal to the microprocessor, microcontroller or other suitable processor, stores one or more programs/routines for controlling the operation of sleep quality measurement device 2 to enable it to perform the various functions and to implement the methods of operation described in greater detail elsewhere herein (the programs/routines can be in any of a variety of forms such as, without limitation, software, firmware, and the like). More specifically, as seen in FIG. 1, processing unit 12 includes at least an ECG generation module 14 and a sleep assessment module 16, each of which is described in detail below.

ECG generation module 14 is a software module that receives the digital cardiac signal data from analog front end 10 and generates ECG data based thereon using any of a number of well known or hereafter developed techniques/algorithms for generating ECG data from raw cardiac signals. In the exemplary embodiment, that data is stored in memory, which may include a removable memory device such as an SD card, until needed to implement the present invention as described in detail herein.

Sleep assessment module 16 is a software module that receives the ECG data generated by ECG generation module 14, and uses that data to generate a graphical report which indicates the presence or absence of SDB episodes, including sleep apnea, by applying a series of signal processing techniques, described in detail herein in various embodiments, to the ECG data.

In addition, as seen in FIG. 1, sleep quality measurement device 2 also includes a display device 18, such as an LCD, for displaying the graphical report as described herein. Sleep quality measurement device 2 may also be coupled, in a wired (e.g., via USB) manner or wirelessly, to a printer (not shown) so that the graphical report can also be printed if desired. Finally, sleep quality measurement device 2 includes an input device 20, such as a keyboard/keypad, that enables information (e.g., control and/or operational information) to be input into processing unit 12. In one particular embodiment, display device 18 and input device 20 may be combined in, for example, a touch screen or the like.

Figure 2:
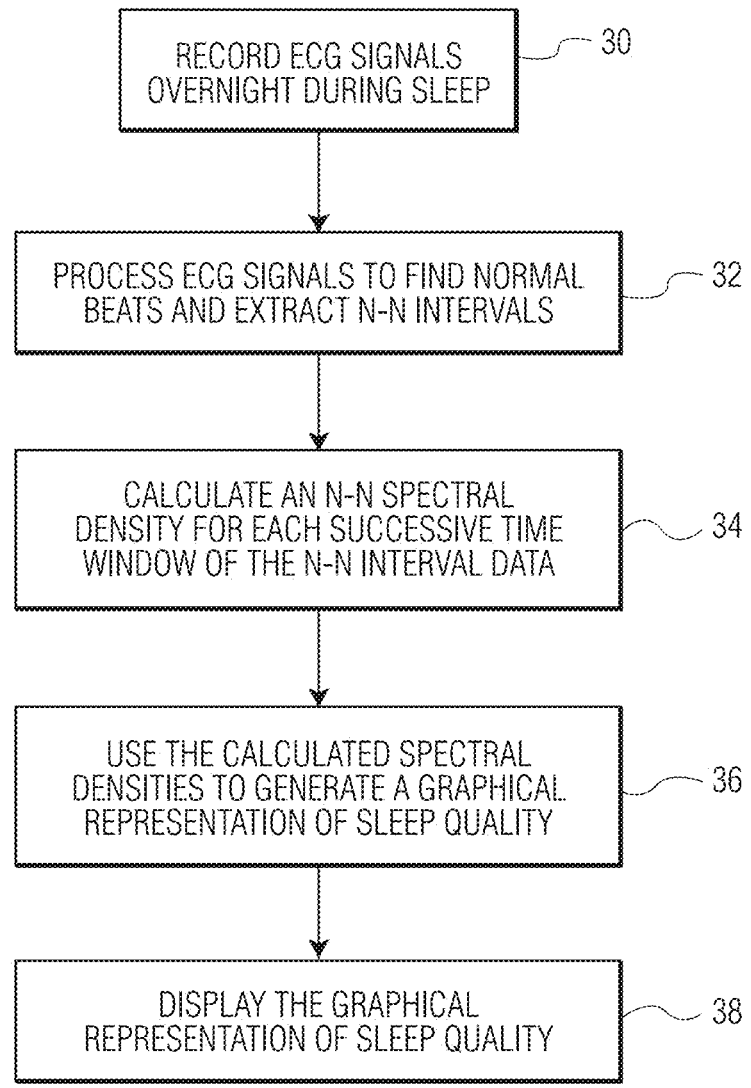
FIG. 2 is a flowchart illustrating a method of generating a graphical representation of sleep quality based on ECG data according to one exemplary embodiment of the present invention.

FIG. 2 is a flowchart illustrating a method of generating a graphical representation of sleep quality based on ECG data according to one exemplary embodiment of the present invention. As noted elsewhere herein, in the present embodiment, the method of FIG. 2 is implemented in one or more software routines stored in and executable by processing unit 12. The method begins at step 30, wherein ECG data for patient 8 is recorded (collected and stored) by sleep quality measurement device 2 overnight while patient 8 is sleeping. As described elsewhere herein, this is primarily accomplished by ECG signal generating module 14 via wires 6A and 6B and electrodes 4A and 4B. As is well known in the art, ECG provides a convenient measurement of the electrical activity of the heart, wherein each cardiac cycle in an ECG signal is characterized by successive waveforms, known as a P wave, a QRS complex and a T wave. These waveforms represent the polarization and repolarization activities in the cells of the atrium and ventricle of the heart. Once all of the overnight ECG data is recorded, the method proceeds to steps 32-38, which are, in the exemplary embodiment, implemented in sleep assessment module 16 and described below.

At step 32, the ECG data is processed to identify normal beats in the ECG data and then extract the N-N intervals of the identified normal beats. As used herein, the term "normal beat" shall mean a normal QRS complex. More specifically, in the exemplary embodiment, the method at step 32 analyzes the ECG data using an ECG beat detection and classification algorithm to classify each of the QRS complexes in the recorded ECG data as either normal or abnormal. In this context, the family selected to represent the "normal" includes the morphology most frequently seen which is neither premature nor wider than its neighbors. Thus, in step 32, every ECG beat in the recorded ECG data is analyzed using the same beat classification rules and classified as either normal or abnormal. Abnormal beats, for example, may include ventricular, paced, and questionable beats. In the exemplary embodiment, the beat classification rules use a combination of one or more of the following information: (i) feature measurements, (ii) timing/rhythm, (iii) template matching, (iv) morphology similarity to neighboring beats, and (v) pace pulses associated with the beat (if patient 8 is paced). The classification rules try to emulate the behavior a clinician uses when analyzing an ECG waveform to classify beats. Furthermore, as used herein, the term "N-N interval" shall mean the time lapse between the peaks (the "R" point) of the QRS complexes of two successive normal beats.

Thus, following step 32, the method will have determined a number of N-N intervals for the ECG data, with each of the N-N intervals being associated with a particular time in the ECG data. In addition, the calculated N-N intervals may be segregated into a number of time windows (which may overlap), wherein each window includes a number of the calculated N-N interval values. In the exemplary embodiment, the time windows are sliding windows defined by "x time window sliding y," meaning that each window will be x minutes (or some other unit of time) in length, and the next successive window will be spaced over y minutes (or some other unit of time). The parameters x and y can have different values based on user configuration. In addition, each window length x will be centered at a time instant referred to herein as "x-mid." In the non-limiting, exemplary embodiment used herein to describe the present invention, x equals six minutes and y equals one minute, and thus the first window would be 0 to 6 minutes ("x-mid=3"), the second window would be 1 to 7 minutes ("x-mid=4"), and so on. In addition, the N-N intervals for each widow may be plotted v. time. FIG. 2 shows two such plots, labeled 40A and 40B, for the exemplary embodiment, wherein plot 40A is for the time window from 47 minutes to 53 minutes with x-mid=50, and the plot 40B is for the time window from 147 minutes to 153 minutes with x-mid=150.

Figure 3:
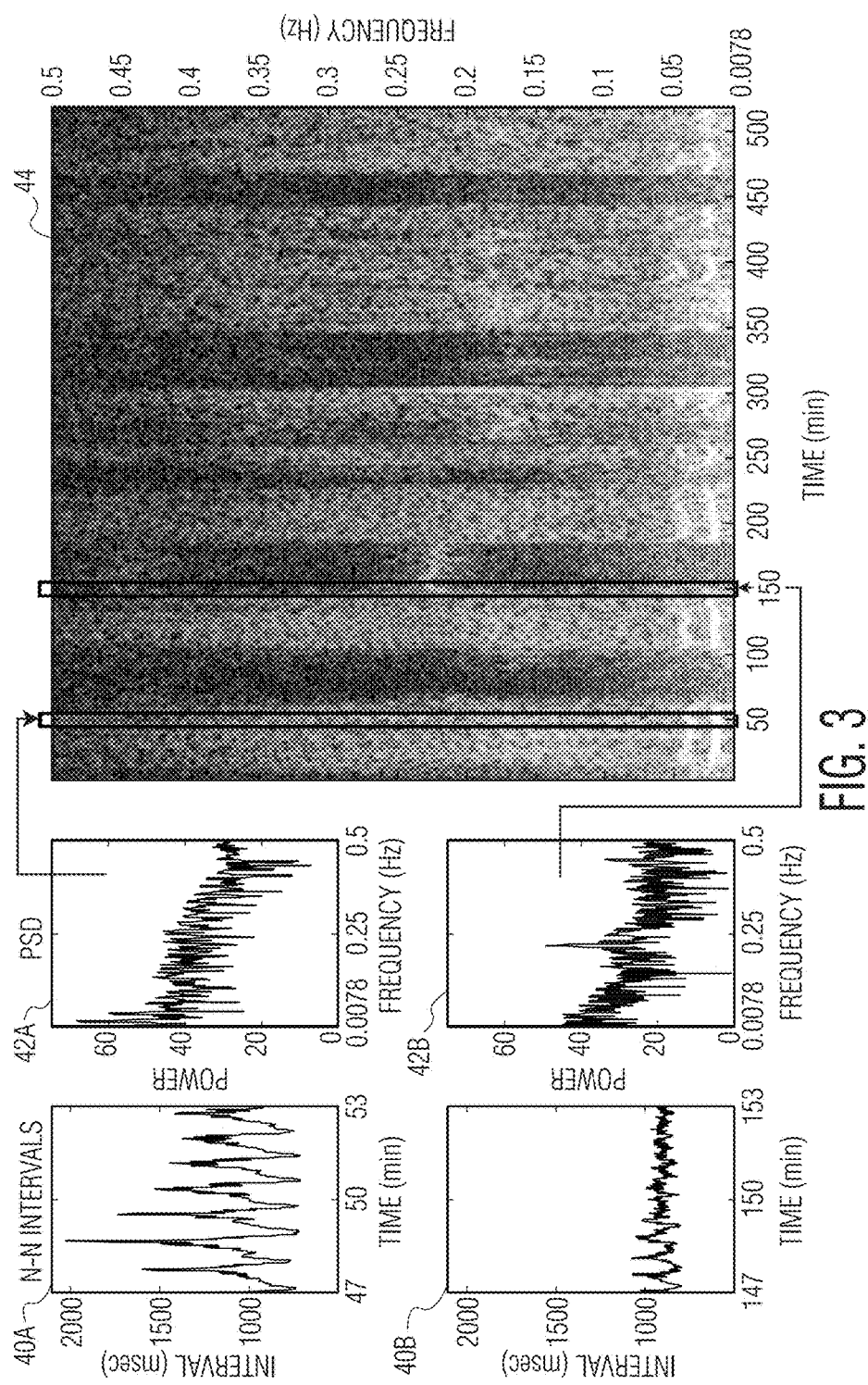
FIG. 3 illustrates how an example graphical representation of sleep quality may be generated using the method of FIG. 2.

Next, the method proceeds to step 34, wherein for each successive time window described above, an N-N spectral density is calculated from the N-N interval data using a suitable spectral estimation method, such as Fourier analysis (e.g., FFT) or least-squares spectral analysis (LSSA), also known as Lomb technique. As used herein, the term "spectral density" shall mean a positive real function of a frequency variable associated with a stationary stochastic process, or a deterministic function of time, which has dimensions of power per hertz (Hz), or, alternatively, energy per hertz, and which measures the frequency content of a stochastic process and helps identify periodicities therein. Spectral density may also be called power spectral density (PSD) (as in the exemplary embodiment shown in FIG. 3), energy spectral density (ESD), or simply the spectrum or power spectrum of a signal. Each calculated N-N spectral density may be represented as a 2-D plot of frequency (x-axis) v. power (y-axis). FIG. 3 shows two such PSD plots, labeled 42A and 42B, for the exemplary embodiment, wherein plot 42A is for the time window from 47 minutes to 53 minutes with x-mid=50, and the plot 42B is for the time window from 147 minutes to 153 minutes with x-mid=150. In addition, because each time window has a calculated N-N spectral density associated with it, each x-mid value will therefore also have a calculated N-N spectral density associated with it. The significance of this is described below.

Next, the method proceeds to step 36, wherein the calculated N-N spectral densities are used to generate a graphical representation of sleep quality. In the exemplary embodiment, the graphical representation of sleep quality is shown in FIG. 3 (labeled item 44) and is a plot of time (x-axis) v. frequency (y-axis), wherein the graphical representation 44 is generated in the following manner. As noted above, each x-mid value in the time windows has a calculated N-N spectral density associated with it, and that N-N spectral density is used to create a vertical image in the graphical representation that is: (i) positioned at the associated x-mid, (ii) has a width of minute (or some other value as determined by the particular user configuration; this width is the y from "x time window sliding y" described above), and (iii) has a height of the frequency range of the calculated N-N spectral densities. In addition, in each vertical image, the particular color at each frequency value along the y-axis is determined based on the associated power at that frequency from the spectral density (in each spectral density there is one power value for each frequency in the frequency range). In other words, to create the vertical image at any x-mid point, each power in the spectral density associated with the x-mid is converted to a corresponding color (based on some predetermined scale), and that color is placed along the vertical (y) axis at the associated frequency value. The colors used in the vertical images could be grayscale colors (i.e., different shades of gray ranging from black (weakest intensity) to white (strongest intensity)) (FIG. 3), or, alternatively, colors from a full color scale. The completed vertical image is then positioned as described above.

Putting each of the one-minute-wide vertical images next to each other on their corresponding locations (the associated "x-mid" points) generates the full graphical representation 44 as shown in FIG. 3. Furthermore, FIG. 3 illustrates the positioning of the vertical images for the spectral density associated with the plots 42A and 42B (x-mid equal to 50 and 150, respectively). As a result, graphical representation 44 in this embodiment may be thought of as image in which the x-axis is time, the y-axis is frequency, and the color at each time instant "x-mid" is the "power" of the spectral density at that time instant.

Following step 36, the method proceeds to step 38, wherein the generated graphical representation 44 is displayed on display device 18. In addition to or instead of displaying graphical representation 44, graphical representation 44 may be printed as described elsewhere herein.

Figure 4:
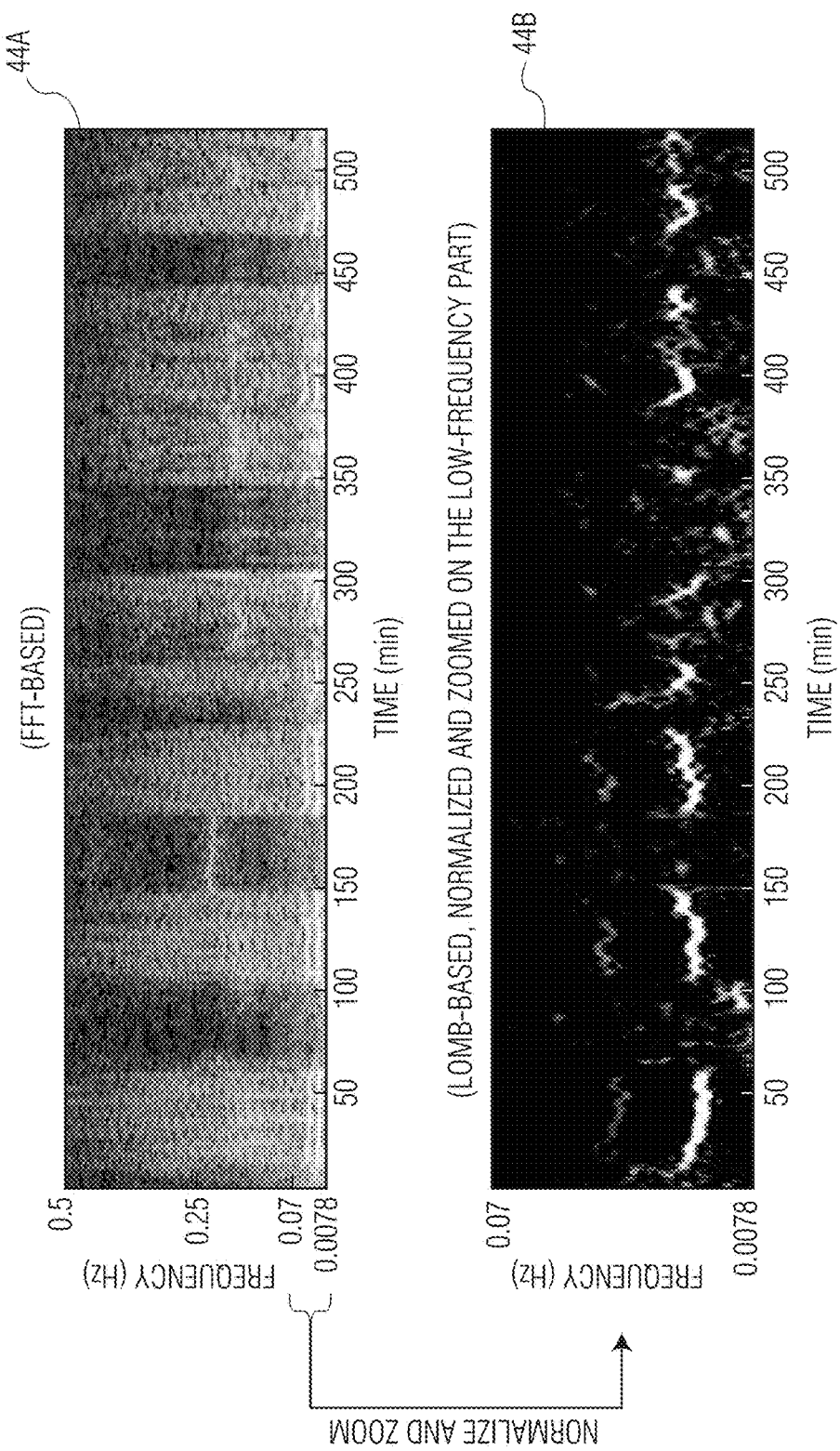
FIG. 4 shows example graphical representations of sleep quality generated using the method of FIG. 2 for a person suffering from SDB.

In one particular exemplary embodiment, in step 34, for each successive time window, two N-N spectral densities are calculated from the N-N interval data, each using a different spectral estimation method. In particular, in this embodiment, the N-N spectral densities are calculated using (i) an FFT method, and (ii) the Lomb method. Then, in step 36, the two sets of spectral densities are independently used to create two different graphical representations, shown in FIG. 4, in the manner described elsewhere herein. More specifically, the FFT-based spectral densities are used to create the top graphical representation 44A, and the Lomb method-based spectral densities are used to create the bottom graphical representation 44B. As seen in FIG. 4, graphical representation 44A covers the whole frequency range, while graphical representation 44B focuses only on the narrow frequency range that includes the most useful information for apnea screening, namely the lower-frequency part. Since the Lomb method generates normalized power spectra, graphical representation 44B is normalized and zoomed on the lower-frequency part. Alternatively, one can create an additional graphical representation by normalizing and zooming on the lower frequency part in graphical representation 44A.

Again, it is to be understood that the above described particular embodiment is just an example, and that the present invention contemplates the use of techniques different than FFT or Lomb, that a graphical representation may zoom on a different region, and/or that spectral densities may be normalized differently.

Figure 5:
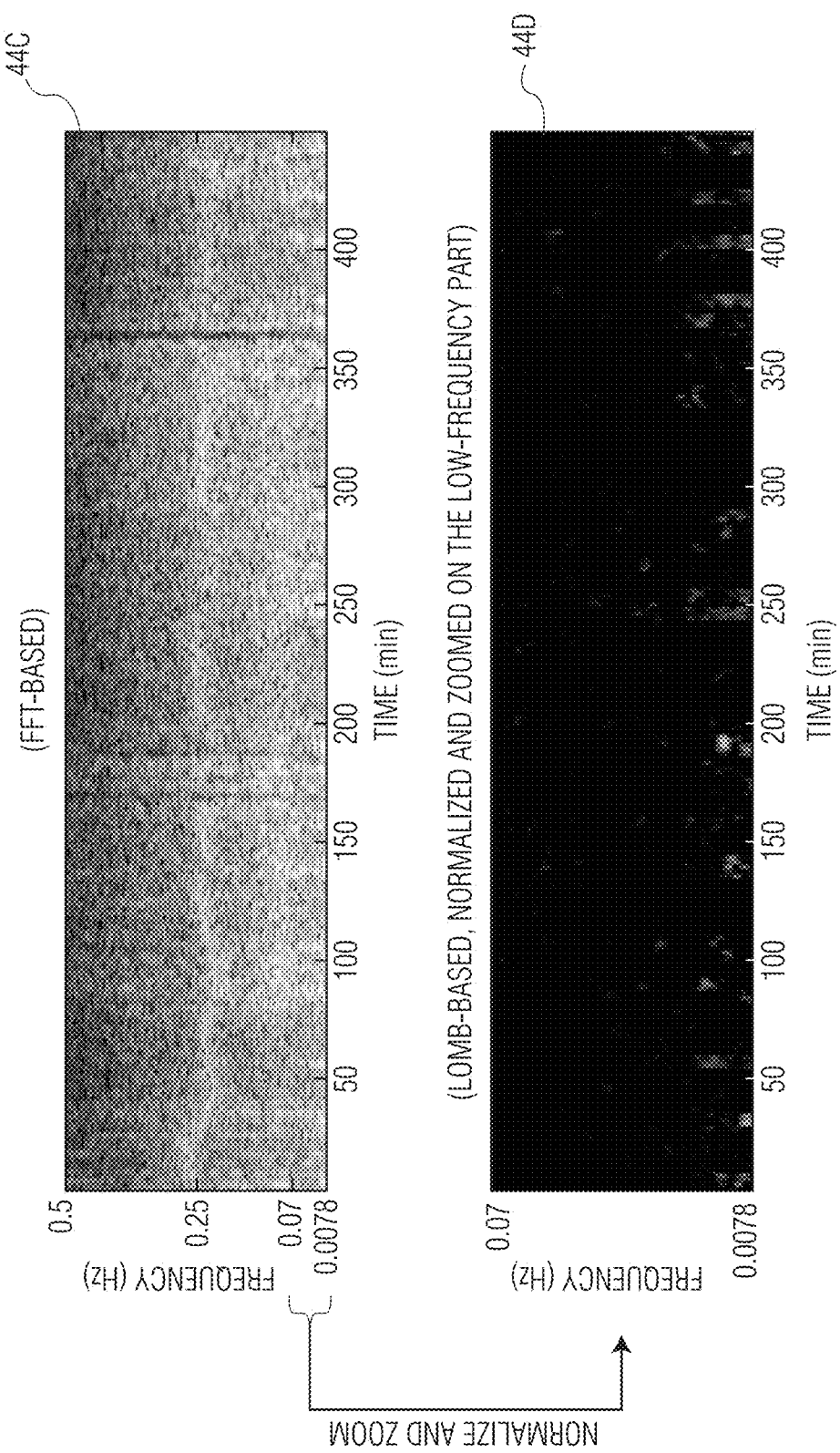
FIG. 5 shows further additional example graphical representations of sleep quality generated using the method of FIG. 2 for a healthy person (not suffering from SDB)

To get a sense of the sleep quality, one can look at graphical representations 44 to examine the homogeneouity in the lower frequency part of the diagram. For example, the white bands in the graphical representation 44A and graphical representation 44B shown on FIG. 4 (more visible in the bottom plot) indicate low-frequency oscillations in the heart rate which is due to sleep apnea. Therefore, the presence of many of them in this example means the patient's sleep quality has been low, since frequent epochs of sleep apnea occurred during asleep. In contrast, FIG. 5 shows graphical representation 44C and graphical representation 44D associated with a healthy person (i.e., a person not experiencing SDB) with very few epochs and nearly zero sleep apnea epochs. It can be seen that, for this example, the lower-frequency part of each of the graphical representations 44C, 44D is rather homogeneous and does not have many white bands.

Figure 6:
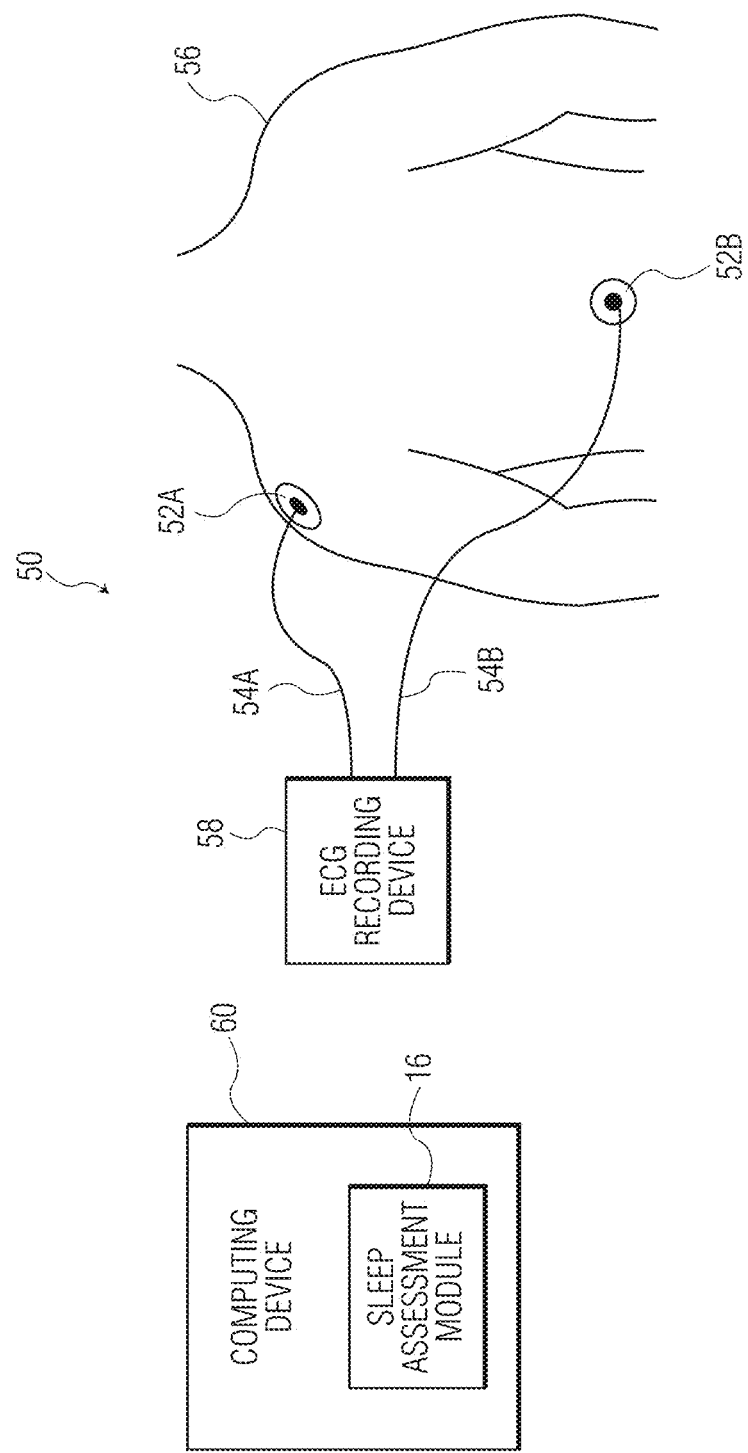
FIG. 6 is a schematic diagram showing a sleep quality measurement system according to an alternative exemplary embodiment of the invention.

FIG. 6 is a schematic diagram showing a sleep quality measurement system 50 according to an alternative non-limiting, exemplary embodiment of the invention. In the illustrated, non-limiting embodiment, sleep quality measurement system 50 employs single lead/channel ECG detection and includes electrodes 52A and 52B coupled to wires 54A, 54B, respectively for collecting cardiac signals from a patient 56. It will be understood, however, that this is meant to be exemplary only, and that present embodiment, like the embodiment of FIG. 1, may employ more than single lead/channel ECG detection as described elsewhere herein. In addition, sleep quality measurement system 50 includes ECG recording device 58, which may be any type of known or hereafter developed apparatus for generating and recording at least one channel of ECG data based on cardiac signals collected by wires 54A, 54B via electrodes 52A, 52B. For example, and without limitation, ECG recording device 58 may be a polysomnography device that includes one or two channels of ECG, a Holter monitor, a hospital bedside ECG monitor, or a mobile cardiac outpatient telemetry (MCOT) monitor.

As seen in FIG. 6, sleep quality measurement system 50 also includes a computing device 60, such as a personal computer or a server computer, which includes sleep assessment module 16 as described herein. Thus, the ECG data that is recorded by ECG recording device 58 (for example in step 30 of FIG. 2), may be provided to computing device 60 and a graphical representation 44 may be created based on that data by sleep assessment module 16 as described elsewhere herein using the method of FIG. 2. As will be appreciated, the ECG data that is recorded by ECG recording device 58 may be provided to computing device 60 in any of a number of ways, such as by a wired (e.g., USB) or wireless connection between ECG recording device 58 and computing device 60, or by transfer using a portable memory device, such as an SD card, a USB drive, or a compact disc. In addition, computing device 60 may display and/or print the generated graphical representation 44 for review by a clinician.

Thus, the present invention, in the various exemplary embodiments described herein, provides a simple, low cost and non-invasive method for assessing sleep quality and visualizing SDB that is based on at least one channel of ECG data.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing a graphical representation of sleep quality, comprising:
    obtaining ECG data for a patient in a sleep assessment module of a computer processing unit;
    obtaining a plurality of N-N intervals from the ECG data in the sleep assessment module by processing the ECG data to identify a plurality of normal beats and extracting the plurality of N-N intervals based on the identified normal beats;
    calculating in the sleep assessment module a plurality of spectral densities based on the plurality of N-N intervals, wherein each spectral density is associated with one of a plurality of successive time windows and is calculated based on certain ones of the N-N intervals associated with the one of the plurality of successive time windows;
    generating the graphical representation of sleep quality in the sleep assessment module based on the plurality of spectral densities by creating the graphical representation as a plot having a time axis and a frequency axis, wherein the graphical representation includes a plurality of images with each image being created based a respective one of the spectral densities by color coding each image in a manner wherein a particular color at each frequency value along the frequency axis is determined based on an associated power at that frequency from the spectral density from which the image was created; and
    displaying the graphical representation on a display device.

2. The method according to claim 1, wherein the obtaining ECG data for the patient comprises at least one of: (i) collecting cardiac signals from the patient and generating the ECG data based on the cardiac signals, or (ii) receiving the ECG data within a module structured to perform the steps of obtaining the plurality of N-N intervals, calculating the plurality of spectral densities, and generating the graphical representation.

3. The method according to claim 1, wherein each image in the graphical representation has a length along the frequency axis equal to a frequency range of the spectral densities.

4. The method according to claim 1, wherein the plurality of spectral densities cover a first frequency range and are calculated based on a first technique, wherein the method further comprises: (i) calculating a plurality of second spectral densities based on the plurality of N-N intervals, wherein each second spectral density is associated with one of a plurality of second successive time windows and is calculated based on certain ones of the N-N intervals associated with the one of the plurality of second successive time windows based on a second technique different than the first technique such that the plurality of second spectral densities cover only a second frequency range including only a lower portion of the first frequency range, and (ii) generating a second graphical representation of sleep quality based on the plurality of second spectral densities that covers only the second frequency range.

5. A sleep quality measurement apparatus, comprising a processing unit having a sleep assessment module and one or more routines executable by the processing unit and structured to:
    obtain in the sleep assessment module a plurality of N-N intervals from ECG data generated from cardiac signals collected from a patient by processing the ECG data to identify a plurality of normal beats and extracting the plurality of N-N intervals based on the identified normal beats;
    calculate in the sleep assessment module a plurality of spectral densities based on the plurality of N-N intervals, wherein each spectral density is associated with one of a plurality of successive time windows and is calculated based on certain ones of the N-N intervals associated with the one of the plurality of successive time windows;
    generate in the sleep assessment module a graphical representation of sleep quality based on the plurality of spectral densities by creating the graphical representation as a plot having a time axis and a frequency axis, wherein the graphical representation includes a plurality of images with each image being created based a respective one of the spectral densities by color coding each image in a manner wherein a particular color at each frequency value along the frequency axis is determined based on an associated power at that frequency from the spectral density from which the image was created; and
    cause the graphical representation to be displayed on a display device.

6. The sleep quality measurement apparatus according to claim 5, further comprising means for collecting the cardiac signals from the patient.

7. The sleep quality measurement apparatus according to claim 5, wherein the successive time windows are sliding time windows defined by x time window sliding y, meaning that each time window will be x units in length, and each successive time window will be spaced y units from a beginning of the time window immediately preceding it.

8. The sleep quality measurement apparatus according to claim 5, wherein each image in the graphical representation has a length along the frequency axis equal to a frequency range of the spectral densities.

9. The sleep quality measurement apparatus according to claim 5, wherein the plurality of spectral densities cover a first frequency range and are calculated based on a first technique, wherein the one or more routines are further structured to: (i) calculate a plurality of second spectral densities based on the plurality of N-N intervals, wherein each second spectral density is associated with one of a plurality of second successive time windows and is calculated based on certain ones of the N-N intervals associated with the one of the plurality of second successive time windows based on a second technique different than the first technique such that the plurality of second spectral densities cover only a second frequency range including only a lower portion of the first frequency range, and (ii) generate a second graphical representation of sleep quality based on the plurality of second spectral densities that covers only the second frequency range.

10. A method of providing a representation of sleep quality, comprising:
    obtaining ECG data for a patient in a sleep assessment module of a computer processing unit;
    obtaining a plurality of N-N intervals from the ECG data in the sleep assessment module by processing the ECG data to identify a plurality of normal beats and extracting the plurality of N-N intervals based on the identified normal beats;

calculating a plurality of first spectral densities based on the plurality of N-N intervals in the sleep assessment module, wherein each first spectral density is associated with one of a plurality of first successive time windows and is calculated based on certain ones of the N-N intervals associated with the one of the plurality of first successive time windows;

calculating a plurality of second spectral densities based on the plurality of N-N intervals in the sleep assessment module, wherein each second spectral density is associated with one of a plurality of second successive time windows and is calculated based on certain ones of the N-N intervals associated with the one of the plurality of second successive time windows;

generating in the sleep assessment module a composite graphical representation including a first graphical representation of sleep quality generated based on the plurality of first spectral densities and a second graphical representation of sleep quality generated based on the plurality of second spectral densities, wherein the first spectral densities cover a first frequency range, wherein the first graphical representation is generated to covers an entirety of the first frequency range, and wherein the second graphical representation is normalized and is generated to covers only a portion of the first frequency range; and displaying the graphical representation on a display device.

11. The method according to claim 10, wherein the obtaining ECG data for a patient comprises at least one of: (i) collecting cardiac signals from the patient and generating the ECG data based on the cardiac signals, or (ii) receiving the ECG data within a module structured to perform the steps of obtaining a plurality of N-N intervals, calculating the plurality of spectral densities, and generating the graphical representation.

12. The method according to claim 10, wherein the graphical representation is a plot having a time axis and a frequency axis.

13. The method according to claim 12, wherein each of the plurality of first time windows has an associated mid value representing a middle of the time window such that each first spectral density is associated with one of the mid values, and wherein a plurality of images are created in the first graphical representation, with each image being created based on a respective one of the first spectral densities and being positioned in the first graphical representation along the time axis at a time corresponding to the mid value associated with the respective one of the first spectral densities.

14. The method according to claim 13, wherein each image in the first graphical representation has a length along the frequency axis equal to the first frequency range.

15. The method according to claim 10, wherein the plurality of first spectral densities are calculated based on a first technique, wherein the plurality of second spectral densities are calculated based on a second technique different than the first technique, and wherein the plurality of second spectral densities cover only a second frequency range including only a lower portion of the first frequency range.

16. The method according to claim 10, wherein the first graphical representation is a plot having a time axis and a frequency axis, wherein each of the plurality of first time windows has an associated mid value representing a middle of the first time window such that each first spectral density is associated with one of the mid values, wherein a plurality of images are created in the first graphical representation, with each image being created based on a respective one of the first spectral densities and being positioned in the first graphical representation along the time axis at a time corresponding to the mid value associated with the respective one of the first spectral densities, wherein each image in the first graphical representation has a length along the frequency axis equal to the first frequency range, and wherein each image is color coded in a manner wherein a particular color at each frequency value along the frequency axis is determined based on an associated power at that frequency from the first spectral density from which the image was created.

17. A sleep quality measurement apparatus, comprising a processing unit having a sleep assessment module and one or more routines executable by the processing unit and structured to:

obtain in the sleep assessment module a plurality of N-N intervals from ECG data generated from cardiac signals collected from a patient by processing the ECG data to identify a plurality of normal beats and extracting the plurality of N-N intervals based on the identified normal beats;

calculate in the sleep assessment module a plurality of first spectral densities based on the plurality of N-N intervals, wherein each first spectral density is associated with one of a plurality of first successive time windows and is calculated based on certain ones of the N-N intervals associated with the one of the plurality of successive time windows;

calculate in the sleep assessment module a plurality of second spectral densities based on the plurality of N-N intervals, wherein each second spectral density is associated with one of a plurality of second successive time windows and is calculated based on certain ones of the N-N intervals associated with the one of the plurality of second successive time windows; and generate in the sleep assessment module a composite graphical representation including a first graphical representation of sleep quality generated based on the plurality of first spectral densities and a second graphical representation of sleep quality generated based on the plurality of second spectral densities, wherein the first spectral densities cover a first frequency range, wherein the first graphical representation is generated to covers an entirety of the first frequency range, and wherein the second graphical representation is normalized and is generated to covers only a portion of the first frequency range; and cause the graphical representation to be displayed on a display device.

18. The sleep quality measurement apparatus according to claim 17, further comprising means for collecting the cardiac signals from the patient.

19. The sleep quality measurement apparatus according to claim 17, wherein the successive time windows are sliding time windows defined by x time window sliding y, meaning that each time window will be x units in length, and each successive time window will be spaced y units from a beginning of the time window immediately preceding it.

20. The sleep quality measurement apparatus according to claim 17, wherein the graphical representation is a plot having a time axis and a frequency axis.

21. The sleep quality measurement apparatus according to claim 20, wherein each of the plurality of first time windows has an associated mid value representing a middle of the first time window such that each spectral density is associated with one of the mid values, and wherein a plurality of images are created in the first graphical representation, with each image being created based on a respective one of the first spectral densities and being positioned in the first graphical representation along the time axis at a time corresponding to the mid value associated with the respective one of the first spectral densities.

22. The sleep quality measurement apparatus according to claim 17, wherein the plurality of first spectral densities are calculated based on a first technique, wherein the plurality of first spectral densities are calculated based on a second technique different than the first technique, wherein the plurality of second spectral densities cover only a second frequency range including only a lower portion of the first frequency range.

23. The sleep quality measurement apparatus according to claim 17, wherein the first graphical representation is a plot having a time axis and a frequency axis, wherein each of the plurality of first time windows has an associated mid value representing a middle of the time window such that each first spectral density is associated with one of the mid values, wherein a plurality of images are created in the first graphical representation, with each image being created based on a respective one of the first spectral densities and being positioned in the first graphical representation along the time axis at a time corresponding to the mid value associated with the respective one of the first spectral densities, wherein each image in the first graphical representation has a length along the frequency axis equal to the first frequency range, and wherein each image is color coded in a manner wherein a particular color at each frequency value along the frequency axis is determined based on an associated power at that frequency from the first spectral density from which the image was created.

* * * * *